United States Patent [19]
Goodger et al.

[11] Patent Number: 4,457,915
[45] Date of Patent: Jul. 3, 1984

[54] BABESIOSIS VACCINE PREPARED FROM SOLUBLE PARASITIC ANTIGEN FACTORS ISOLATED FROM DISINTEGRATION OF BABESIA INFECTED ERYTHROCITES

[76] Inventors: Brian V. Goodger, "Pine Trees" Mt. Glorious Rd., Mt. Nebo, Brisbane, Queensland; David F. Mahoney, 218 Stanley Ter., Taringa, Brisbane, Queensland; Ian G. Wright, 72 Dewar Ter., Sherwood, Brisbane, Queensland, all of Australia

[21] Appl. No.: 434,539

[22] Filed: Oct. 15, 1982

Related U.S. Application Data

[63] Continuation-in-part of Ser. No. 201,626, Oct. 28, 1980, abandoned.

[30] Foreign Application Priority Data

Nov. 6, 1979 [AU] Australia .............................. PE1217
Aug. 8, 1980 [AU] Australia .............................. PE4950

[51] Int. Cl.³ .......................................... A61K 39/018
[52] U.S. Cl. ............................................... 424/88
[58] Field of Search ........................................ 424/88

[56] References Cited

U.S. PATENT DOCUMENTS 3,511,908  5/1970  Brock et al. .......................... 424/88
3,849,551  11/1974  D'Antonio .......................... 424/88
3,911,097  10/1975  Hanson ................................ 424/88

FOREIGN PATENT DOCUMENTS 403430  10/1968  Australia .............................. 424/88
1030777  5/1966  United Kingdom .................. 424/88

OTHER PUBLICATIONS

Wright et al., Australian Advances in Veterinary Science, 1979, pp. 72–73, "*Babesia bovis* Infections: New Concepts in Vaccination".
Goodger, B. V., (1971), Preparation and Preliminary Assessment of Purified Antigens in the passive . . ., *Aust. Vet. J.* 47: 251–256.
Goodger, B. V., (1973), *Babesia argentina:* Intraerythrocytic Location of Babesial Antigen Extracted . . . , *Int. J. Parasit.* 3: 387–391.
Goodger, B. V., (1976), *Babesia argentina:* Studies on the Nature of an Antigen Associated with Infection, *Int. J. Parasit.* 6: 213–216.
Mahoney, D. F. & Wright, I. G., (1976), *Babesia argentina:* Immunization of Cattle with a Killed Antigen . . . , *Vet. Parasit.* 2: 273, 282.
Mahoney, D. F., Wright, I. G. & Goodger, B. V., (1981), Bovine babesiosis: The Immunization of . . . , *Vet. Immunol. and Immunopathol.*
Ristic, M. & Sibinovic, S., (1964), Equine babesiosis: Diagnosis by a Precipitation in Gel and by . . . , *Am. J. Vet. Res.* 25: 1519–1526.
Sibinovic, S., Sibinovic, K. H., Ristic, M. & Cox, H. W., (1966), Physical and Serologic Properties . . . , *J. Protozool.* 13: 551–553.
Goodger et al., Int. J. Parasitol. 10 (1) (1980): 33–36.
Mahoney et al., Int. J. Parasitol. 9 (4): 297–306; (Aug. 1979).
Goodger et al., Z. Parasitenko, 53 (1) (1977): 47–52.
Mahoney et al., Exp. Parasitol. 32 (1) (1972): 71–85.
Mahoney et al., Australian Vet. J. 55 (1): 10–12 Jan. 1979.
Goodger et al., Austr. J. Exp. Bioc. Med. Sci. 54 (4): 381–390, Aug. 1976.
Goodger, Z. Parasitenko, 48 (1): 1–7 (1975).
Mahoney, Immunity to Animal Parasites, pp. 301–341 (1972).
Smith et al., Am. J. Vet. Res. 40(12): 1678–1682, Dec. 1979, Bovine Babesiosis: Vaccination Against Tick-Borne Challenge Exposure with Culture-Derived *Babesia bovis* Immunogens.
Gravely et al., Vet. Bull. 50(6) #3504 Jun. 1980 of Int. J. Parasitology (1979) 9(6): 591–598, Bovine Babesiosis: Partial Purification and Characterization of Blood Culture-Derived *Babesia bovis*.
James et al., Vet. Bull. 51(7) #4153 Jul. 1981 of Infection & Immunity (1981) 31(1): 358–361, Isolation and Partial Characterization of Culture-Derived Soluble *Babesia bovis* antigens.
Smith et al., Vet. Bull. 51(8) #4965 Aug. 1981 of Science (USA) 212(4492): 335–338, Bovine Babesiosis: Protection of Cattle with Culture-Derived Soluble *Babesia bovis* antigen.

*Primary Examiner*—Shep K. Rose
*Attorney, Agent, or Firm*—Cushman, Darby & Cushman

[57] ABSTRACT

This invention relates to a method of preparation of a babesiosis vaccine which involves treating a suspension of Babesia infected erythrocytes. The erythrocytes are disintegrated, separated into soluble and insoluble fractions and subsequently fibrinogen and contaminated Babesia antigen is removed from the soluble fraction. The residual soluble fraction is then combined with an adjuvant to form the babesiosis vaccine. The invention also includes within its scope a vaccine derived from the abovementioned method and a method of administration of the vaccine to cattle.

42 Claims, No Drawings

BABESIOSIS VACCINE PREPARED FROM SOLUBLE PARASITIC ANTIGEN FACTORS ISOLATED FROM DISINTEGRATION OF BABESIA INFECTED ERYTHROCITES

This application is a continuation-in-part of application Ser. No. 201,626, filed Oct. 28, 1980 and now abandoned.

BACKGROUND OF THE INVENTION

1. Field of the Invention

This invention relates to babesiosis vaccines and their preparation.

2. Description of the Prior Art

Babesiosis is a disease which most domestic animals may experience, and is caused by various species of the tick-borne protozoan parasite Babesia. In the cattle industry in particular, there are many parts of the world where the disease poses serious economic problems. For instance, in Australia during the year 1972 cattle losses directly attributable to the tick-babesiosis disease complex were estimated to be of the order of $42 million.

The only effective vaccines against babesiosis which are currently available involve the use of living organisms, and the production of infection to induce acquired immunity. To avoid the risks inherent in the use of living organisms, vaccines which would confer immunity without infecting the host have been sought for many years. Some success has been obtained by immunization with antigen from the blood of infected animals, but concurrent immunization of the recipients with the blood group antigen has precluded the widescale use of products containing such impurities. The invention described herein concerns a method of preparation of babesiosis vaccine derived from non-living antigenic material but which avoids the shortcomings of earlier art non-living vaccines.

In events leading up to the development of the present invention it was found initially that cattle inoculated with crude suspensions of dead *Babesia bovis* parasites prepared from infected blood were protected against babesiosis even after challenge with strains of virulent organisms. These preparations were unsuitable for practical vaccination because they were contaminated with bovine erythrocytic material, and were likely to cause haemolytic anaemia in the calves of vaccinated cows due to the production of incompatible blood-group antibodies by the dam and their transfer to the offspring.

However, subsequently to this discovery further efforts were directed towards the purification and characterization of the babesial antigens contained by infected red cells that confer protection against babesiosis on uninfected cattle. A number of different babesial antigens were identified in the infected red cell and on the surface of the parasite itself. The first was a soluble antigen present in the red cell cytoplasm and released with the haemoglobin when the infected cell was lysed. As the protective antigens obviously remained in the red cellparasite residue after lysis, this antigen was of no further interest. Sonic disintegration of the insoluble residue after lysis of infected red cells produced a solution that contained two groups of antigens. One group consisted of aggregates of fibrinogen-like protein which contained at least 2 antigenic molecules. One of these antigens was located in a dense band around the rim of the infected erythrocyte and the other was distributed in fine granules on the erythrocyte stroma. The complex was designated the Fibrinogen Associated Antigen (FAA) and was purified from solution by precipitation techniques that were suitable for the isolation of fibrinogen. Thus it was found that one group of antigens consisted of babesial proteins conjugated to fibrinogen molecules to form large aggregates that behaved chemically like fibrinogen and could be purified as such. However, it has now been realised that, surprisingly, another antigen remained in the solution after precipitation and was located on the surface of the parasite. It was not associated with any red cell structure. The fact that this soluble fraction contained an antigen was only discovered after in vivo testing in cattle wherein antibodies were produced after injection of antigen into the host. This in vivo testing was carried out as a final check after the antigen could be not detected by normal serological tests such as haemagglutination. This new antigen is termed Soluble Parasitic Antigen (SPA). It has been found that both FAA and SPA induce protection against *Babesia bovis* infection even though the antibodies produced to each are of different specificity. However, FAA contains the bovine blood group antigens but SPA does not. For this reason SPA is of interest in development as a vaccine for babesiosis.

BRIEF SUMMARY OF THE INVENTION

Thus the present invention is based on the surprising discovery that a soluble fraction obtained on disintegration of babesia infected erythrocytes displays significant and useful antigenic activity. Accordingly, the present invention provides a method of preparation of novel babesiosis vaccine embodying soluble antigenic factors isolated from the product of disintegration of babesia infected erythrocytes. The present invention also includes within its scope the aforementioned vaccine.

In broad terms the method of the invention includes the following steps:

(i) disintegration of a suspension of babesia infected erythrocytes:

(ii) separation of the soluble and insoluble fractions contained in the disintegrated erythrocyte suspension;

(iii) removal of fibrinogen and contaminated babesial antigen from the soluble fraction of the disintegrated erythrocyte suspension;

The product of step (iii) may then be combined with a suitable adjuvant for administration purposes.

The suspension of erythrocytes used in step (i) may be prepared by various methods known in the art, such as that described by Mahoney (Exp. Parasitol. 20 232–241). Preferably at least 95% of cells in the suspension should be infected with *Babesia bovis*.

The cells may conveniently be disrupted in a sonic disintegrator. Separation of the soluble and insoluble fractions produced by cell disruption may be readily achieved by centrifugation at about 145,000 g for 60 minutes. Subsequently the supernatant of the centrifuged suspension may have contaminants such as haemoglobin removed by methods known in the art. Thus for example haemoglobin may be absorbed onto CM Sephadex (Dozy and Huisman; J. Chrom 40, 62–70). If desired, the removal of the haemoglobin may be omitted. Haemoglobin does not interfere with the antigenic activity of the material. However, it is the source of a deep red colour which may be aesthetically unacceptable.

In step (iii) as referred to above, the removal of fibrinogen and contaminated babesial antigen is an important part of the present invention. One suitable method involves precipitation with thrombin and calcium chloride (Goodger; Int. J. Parasitol 6, 213-216).

The product of the above procedures has been found to contain specific antigens of *Babesia bovis* free of contaminants, and when administered in combination with appropriate adjuvants is effective in inducing protection against subsequent challenge with *Babesia bovis*.

The oil based adjuvants are of value as components in the vaccines of this invention and include Freunds Complete Adjuvant (FCA), Freunds Incomplete Adjuvant, Adjuvant 65, Wellcome Mineral Oil Adjuvant. Saponin aqueous solution may also be used as adjuvant.

The invention also offers a method of immunizing animals against *Babesia bovis*. Essentially the method comprises administering to animals, a vaccine as described herein. Typically, an immunization regime according to the method would involve intramuscular (i/m) inoculation three times at fourteen day intervals with 5.0 ml of the vaccine giving an antibody titre in excess of 1/6400 in the passive haemagglutination test (Goodger; Aust. vet. J. 47, 251-256).

DETAILED DESCRIPTION OF THE PREFERRED EMBODIMENTS

The invention will now be described with reference to the following examples:

Example 1

Vaccine Preparation

Infected erythrocytes were concentrated from infected blood to approximately 95% suspension by differential lysis on the non-infected cells in a hypotonic salt solution. The infected erythrocytes were then suspended in phosphate buffered saline (PBS), pH 7.2, at a concentration of $5 \times 10^9$/ml and were disrupted in a sonic disintegrator operating at 100-150 w for four minutes. This material, designated infected erythrocytic antigen (IEA), was stored in the vapour phase of liquid nitrogen. Before use, it was frozen and thawed three times and fractionated as follows: a crude soluble extract (CSE) was the supernatant fluid obtained by centrifugation of IEA at 145,000 g for sixty minutes. CSE was then passed through two fractionation steps. The first was to remove haemoglobin with CM Sephadex (Doxy and Huisman, 1969) and the second was to precipitate the fibrinogen-associated antigens (FAA) of *Babesia bovis*. The method used involved the precipitation of fibrinogen at 37° C. by mixing CSE with either equal volumes of a solution containing 0.05 $CaCl_2$ and 20 units of thrombin per ml or with 0.1% aqueous protamine sulphate in proportion 2;1 (v/v). The insoluble precipitate was discarded and the residual supernatant fluid after precipitation of FAA was designated the soluble parasitic extract (SPE).

Example 2

Use of Vaccine

Cattle 2-3 years of age, were purchased in a Babesia-free area and were maintained under conditions that precluded accidental babesial infection. SPE was emulsified with an equal quantity of Freund's Complete Adjuvant and 5 ml of the mixture was inolulated into each of the cattle intramuscularly (i/m). Three doses were given, each two weeks apart. A control group, equal in number to that inoculated with SPE were inoculated with the adjuvant alone.

Two to four weeks after the last injection, the cattle were infected by the (i/v) inoculation of $10^8$ erythrocytes infected with a virulent strain of *Babesia bovis*. Protection was assessed on the differences in levels of parasitaemia measured by counting the number of organisms/$mm^3$ in jugular blood, falls in packed cell volume (PCV) and rises in rectal temperature between immunized and control groups. After challenge the control group showed severe clinical illness, and 40% of the animals died between nine and ten days after inoculation. The animals in the immunized group showed slightrises in rectal temperature but no other overt signs of disease. No deaths occured and the differences in falls in PCV between immunized and control groups became significant (P 0.05) on day 7, and increased until the surviving control animals commenced to recover after day 11. Levels of parasitaemia in the immunized animals were also significantly lower than that in the controls (P 0.01).

The vaccine referred to above in Examples 1 and 2 was prepared from a virulent strain of *Babesia bovis* known as Samford or "S" strain. The virulent strain was maintained as a stabilate in liquid nitrogen as is known in the art.

However, it will also be appreciated that the vaccine of the invention may be derived from avirulent strains of *Babesia bovis*. The virulent strain referred to above may be converted into an avirulent strain by standard techniques as is known in the art. For example a gamma-radiation technique may be used as described in *Int. J. of Parasitology* 3, 209-217 (1973).

It has also been discovered that vaccines derived from avirulent strains are just as protective as vaccines derived from virulent strains. Thus avirulent strains derived from a parent virulent strain was proven to be equally effective (*See Aust. Vet. J.* 55 10-12 (1979).

It is also known that Babesia parasites are normally morphologically divided into large and small types which affect a common host. For example, *B. caballi* is the species name for a large type parasite which occurs in horses and *B. equi* is the species name for the small type parasite which occurs in horses. Similarly, *B. ovis* is the species name of the large type parasite which occurs in dogs, and *B. gibsoni* is the species name of the small type parasite which occurs in dogs. *B. ovis* is the small type parasite that occurs in sheep. The method of the invention is species specific. Thus, as is well understood in the art, inoculation with a vaccine prepared from soluble antigen factors isolated from a given species of Babesia will only provide protection against that species, and will not provide protection against a different species. Nevertheless, the presently claimed invention is applicable to various species of Babesia which have much in common. Protection against a given species may be obtained using antigen factors isolated from erythrocytic material infected with that species. The invention may be operable against various species of Babesia including *B. equi, B. gibsoni, B. bovis*, and *B. ovis*.

The term "strain" when applied to various species of Babesia parasite is used in a very loose sense. Conventional serological tests do not indicate any difference between the various "strains" of a common species. Normally one "strain" of a Babesia species differs from others only in the location where it was geographically isolated. The present invention is not "strain" specific. On the contrary, inoculation with one "strain" of a given species will provide protection against all "strains" of that species.

As examples of strains of *B. bovis* which may be used to prepare vaccines of the invention there may be mentioned the Samford, Lismore, Cannon Hill and Glenlogan strains, which are both virulent and avirulent.

It will also be appreciated that the term "disentegrated" or "disintegration" includes within its scope the following:
(1) osmotic lysis wherein the cell membrane may be disrupted in solutions of weak ionic strength,
(2) mechanical lysis e.g. sonic disentegration,
(3) proliferation of parasites within the cell and exiting from the cell causing breakdown of the cell membrane,
(4) cell lysis wherein erythrocytes may be lysed by specific lysins or cell antibodies.

From the techniques described above the soluble and insoluble fractions may be subsequently separated as previously described. Thus, if desired, Babesia parasites may be grown or cultivated in cell culture and the cells may be subsequently lysed to obtain the desired soluble antigenic fraction.

Example 3

From Example 1 above the soluble parasitic extract (SPE) was compared to the following strains of Babesia bovis which were used to infect erythrocytes wherein such erythrocytes were subsequently disrupted by a procedure similar to that described in Example 1.
(i) Lismore (L) virulent
(ii) Lismore (L) avirulent
(iii) Samford (S) virulent
(iv) Samford (S) avirulent
(v) Cannon Hill (C) virulent
(vi) Strain K (isolated by Queensland Government Department of Primary Industries, Brisbane, Australia) virulent
(vii) Strain K avirulent.

It was discovered that the abovementioned strains were found to have antigens in common with SPE by the demonstration of common serological behaviour using radio immunoassay techniques (RIA) indirect fluorescent antibody (IFA) or ELISA techniques.

We claim:
1. A method of preparation of a babesiosis vaccine, including the steps of:
   (i) disintegrating a suspension of *Babesia bovis* infected erythrocytes;
   (ii) separating the soluble and insoluble fractions contained in the disintegrated erythrocyte suspension;
   (iii) removing fibrinogen and contaminated babesial antigen from the soluble fraction of the disintegrated erythrocyte suspension; and
   (iv) combining the soluble fraction after step (iii) with an adjuvant to form the babesiosis vaccine.
2. A method as claimed in claim 1 wherein in the suspension at least 95% of cells therein are infected with *Babesia bovis*.
3. A method as claimed in claim 1 or 2 wherein the erythrocytes are disintegrated in a sonic disintegrator.
4. A method as claimed in claim 3 wherein the separation of the soluble and insoluble fractions contained in the disintegrated erythrocyte suspension is achieved by centri- fugation.
5. A method as claimed in claim 4 wherein the centrifugation is carried out at about 145,000 g for sixty minutes.
6. A method as claimed in claims 1 or 2 wherein haemoglobin is removed from the soluble fraction after step (ii).
7. A method as claimed in claim 6 wherein haemoglobin is absorbed onto CM Sephadex.
8. A method as claimed in claims 1 or 2 wherein the fibrinogen and contaminated babesial antigen is removed by precipitation with thrombin and calcium chloride.
9. A vaccine whenever prepared by a process as claimed in claims 1 or 2.
10. A vaccine for administration to cattle including: a soluble fraction derived from a disintegrated suspension of *Babesia bovis* infected erythrocytes and having fibrinogen and contaminated babesial antigen removed therefrom; and an adjuvant.
11. A method of treatment of cattle including the step of administration to the cattle of a vaccine as claimed in claims 9 or 10.
12. A method according to claim 3 wherein the erythrocytes are disintegrated in a sonic disintegrator.
13. A method according to claim 12 wherein the separation of the soluble and insoluble fractions contained in the disintegrated erythrocyte suspension is achieved by centrifugation.
14. A method according to claim 13 wherein the centrifugation is carried out at about 145,000 g for sixty minutes.
15. A method according to claim 2 wherein haemoglobin is removed from the soluble fraction after step (ii).
16. A method according to claim 15 wherein haemoglobin is absorbed onto CM Sephadex.
17. A method according to claim 2 wherein the fibrinogen and contaminated babesial antigen is removed by precipitation with thrombin and calcium chloride.
18. A vaccine prepared by the process of claim 2.
19. A method of treatment of cattle including the step of administration to the cattle of a vaccine of claim 10.
20. A method according to claim 1 wherein the babesia infected erythrocytes are virulent *Babesia bovis* infected erythrocytes.
21. A method according to claim 2 wherein at least 95% of the cells therein are infected with virulent *Babesia bovis*.
22. A method according to claim 3 wherein the babesia infected erythrocytes are virulent *Babesia bovis* infected erythrocytes.
23. A method according to claim 4 wherein the babesia infected erythrocytes are virulent *Babesia bovis* infected erythrocytes.
24. A method according to claim 5 wherein the babesia infected erythrocytes are virulent *Babesia bovis* infected erythrocytes.
25. A method according to claim 6 wherein the babesia infected erythrocytes are virulent *Babesia bovis* infected erythrocytes.
26. A method according to claim 7 wherein the babesia infected erythrocytes are virulent *Babesia bovis* infected erythrocytes.
27. A method according to claim 8 wherein the babesia infected erythrocytes are virulent *Babesia bovis* infected erythrocytes.
28. A vaccine according to claim 9 wherein the babesia infected erythrocytes are virulent *Babesia bovis* infected erythrocytes.

29. A vaccine according to claim 10 wherein the babesia infected erythrocytes are virulent *Babesia bovis* infected erythrocytes.

30. A method of treatment of cattle including the step of administering to the cattle a vaccine of claim 29.

31. A method of treatment of cattline including the step of administering to the cattle a vaccine of claim 28.

32. A method of preparation of a babesiosis vaccine including the steps of;
 (i) disintegrating a suspension of erythrocytes infect with the parasite *Babesia bovis* so as to substantially solubilise parasite material contained therein;
 (ii) separating from the resulting mixture a soluble fraction containing essentially parasite material substantially free or erythrocytes;
 (iii) removing fibrinogen and contaminated babesial antigen from said soluble fraction; and
 (iv) combining said soluble fraction with an adjuvant.

33. A method as claimed in claim 32 wherein in the suspension at least 95% of cells therein are infected with *Babesia bovis*.

34. A method as claimed in claim 32 wherein the erythrocytes are disintegrated in a sonic disintegrator.

35. A method as claimed in claim 32 wherein the separation of the soluble and insoluble fractions contained in the disintegrated erythrocyte suspension is achieved by centrifugation.

36. A method as claimed in claim 33 wherein the centrifugation is carried out at about 145,000 g for sixty minutes.

37. A method as claimed in claim 32 wherein haemoglobin is removed from the soluble fraction after step (ii).

38. A method as claimed in claim 37 wherein haemoglobin is absorbed onto CM Sephadex.

39. A method as claimed in claim 32 wherein the fibrinogen and contaminated babesial antigen is removed by precipitation with thrombin and calcium chloride.

40. A vaccine for administration to cattle including a soluble fraction derived from a disintegrated suspension of erythrocytes infected by the parasite *Babesia bovis* containing parasite material substantially free of erythrocyte material and having fibrinogen and contaminated babesial antigen removed therefrom, and an adjuvant.

41. A method according to claim 17 wherein an adjuvant is also administered with the vaccine.

42. A method according to claim 19 wherein an adjuvant is also administered with the vaccine.

* * * * *